US007531716B2

(12) United States Patent
Polston et al.

(10) Patent No.: US 7,531,716 B2
(45) Date of Patent: May 12, 2009

(54) MATERIALS AND METHODS FOR PRODUCING TOMATO YELLOW LEAF CURL VIRUS RESISTANCE IN PLANTS

(75) Inventors: Jane E. Polston, Gainesville, FL (US); Ernest Hiebert, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 294 days.

(21) Appl. No.: 10/477,240

(22) PCT Filed: May 7, 2002

(86) PCT No.: PCT/US02/14481

§ 371 (c)(1), (2), (4) Date: Jun. 10, 2004

(87) PCT Pub. No.: WO02/090509

PCT Pub. Date: Nov. 14, 2002

(65) Prior Publication Data

US 2005/0125862 A1 Jun. 9, 2005

Related U.S. Application Data

(60) Provisional application No. 60/289,315, filed on May 7, 2001, now abandoned.

(51) Int. Cl.
*C12N 15/82* (2006.01)
*C12N 15/87* (2006.01)
*C12N 15/00* (2006.01)
*C07H 21/04* (2006.01)

(52) U.S. Cl. .................... 800/279; 800/280; 536/23.72; 435/320.1

(58) Field of Classification Search ....................... None
See application file for complete search history.

(56) References Cited

U.S. PATENT DOCUMENTS 6,133,505 A 10/2000 Gronenborn
6,291,743 B2 * 9/2001 Stout et al. .................. 800/301

FOREIGN PATENT DOCUMENTS

WO WO 97/39110 10/1997
WO WO 00/43494 A3 7/2000
WO WO 00/43520 A2 7/2000

OTHER PUBLICATIONS

Bendahmane et al 1997, Plant Molecular Biology 33:351-357.*
Bendahmane et al. 1997, Plant Molecular Biology 33:351-357.*
Brunetti et al. 1997, Plant Molecular Biology 33:351-357.*
Noris et al. 1996, Virology 224:130-138.*
Fourgoux-Nicol et al 1999, Plant Molecular Biology 40 :857-872.*
Antignus, Y. et al. "Truncated Rep Gene Originated from *Tomato Yellow Leaf Curl Virus-Israel* [Mild] Confers Strain-Specific Resistance in Transgenic Tomato" *Annals of Applied Biology,* 2004, pp. 39-44, vol. 144.
Brunetti, A. et al. "Transgenically Expressed T-Rep of Tomato Yellow Leaf Curl Sardinia Virus Acts as a *trans*-Dominant-Negative Mutant, Inhibiting Viral Transcription and Replication" *Journal of Virology,* Nov. 2001, pp. 10573-10581, vol. 75, No. 22.
Yang. Y. et al. "Use of *Tomato Yellow Leaf Curl Virus* (TYLCV) *Rep* Gene Sequences to Engineer TYLCV Resistance in Tomato" *Phytopathology,* May 2004, pp. 490-496, vol. 94, No. 5.
European Search Report for Application No. EP 02 74 6353.
An, G. et al. "New cloning vehicles for transformation of higher plants" *EMBO J.* 1985, pp. 277-284, vol. 4, No. 2.
Arguello-Astorga, G.R. et al. "An iteron-related domain is associated to Motif 1 in the replication proteins of geminiviruses: identification of potential interacting amino acid-base pairs by a comparative approach" *Arch. Virol.,* 2001, pp. 1465-1485, vol. 146.
Bendahmane, M. et al. "Engineering Resistance Against Tomato Yellow Leaf Curl Virus (TYLCV) using antisense RNA" *Plant Molecular Biology,* 1997, pp. 351-357, vol. 33.
Brunetti, A. et al. "High Expression of Truncated Viral *Rep* Protein Confers Resistance to Tomato Yellow Leaf Curl Virus in Transgenic Tomato Plants" *Mol. Plant-Microbe Interact,* 1997, pp. 571-579, vol. 10, No. 5.
Cahill, M. et al. "Baseline determination and detection of resistance to imidacloprid in *Bemisia tabaci* (Homoptera: Aleyrodidae)" *Bull. of Ento. Res.,* 1996, pp. 343-349, vol. 86.
Carrer, H. et al. "Targeted Insertion of Foreign Genes into the Tobacco Plastid Genome without Physical Linkage to the Selectable Marker" *Biotechnology,* Aug. 1995, pp. 791-794, vol. 13.
Fauquet, M.C. et al. "Abbreviations for plant virus names—1999" *Arch. Virol.,* 1999, pp. 1249-1273, vol. 144.
Freitas-Astua, J. "Characterization of Resistance In Transgenic Tobacco Plants Expressing Begomoviruses Genes" 2001, pp. 1-99, Ph.D. Dissertation, Gainesville, University of Florida.
Hanson, S.F. et al. "*trans*-Dominant Inhibition of Geminiviral DNA Replication by Bean Golden Mosaic Geminivirus *rep* Gene Mutants" 1999, *Phytopathology,* pp. 480-486, vol. 89.

(Continued)

*Primary Examiner*—Elizabeth F McElwain
*Assistant Examiner*—Li Zheng
(74) *Attorney, Agent, or Firm*—Saliwanchik, Lloyd & Saliwanchik

(57) ABSTRACT

The subject invention concerns materials and methods for providing genetically-engineered resistance in plants to tomato yellow leaf curl geminivirus using a truncated version of the replication associated protein (Rep) gene of TYLCV. Virus-resistant plants produced according to the present invention have horticulturally acceptable phenotypic traits. Methods of the invention comprise transforming a plant with a polynucleotide wherein when the polynucleotide is expressed in the plant, the transformed plant exhibits resistance to plant viral infections. An exemplified embodiment utilizes a polynucleotide comprising a truncated Rep gene derived from a Florida isolate of TYLCV-Is. The methods of the invention can be used to provide resistance to TYLCV infection in plants such as tomato and tobacco. The present invention also concerns transformed and transgenic plants and plant tissue that express a polynucleotide comprising a truncated Rep gene of TYLCV.

46 Claims, 5 Drawing Sheets

OTHER PUBLICATIONS

Hong, Y. et al. "Virus Resistance in *Nicotiana benthamiana* Conferred by African Cassava Masaic Virus Replication-Associated Protein (AC1) Transgene" 1996, *Mol. Plant-Microbe Interact,* pp. 219-225, vol. 9, No. 4.

Kelemen, Z. et al. "Transformation Vector Based on Promoter and Intron Sequences of a Replacement Histone H3 Gene. A Tool for High, Constitutive Gene Expression in Plants" *Transgenic Research,* 2002, pp. 69-72, vol. 11.

Lapidot, M. et al. "Effect of Host Resistance on *Tomato Yellow Leaf Curl Virus* (TYLCV) on Virus Acquisition and Transmission by its Whitefly Vector" *Phytopathology,* 2001, pp. 1209-1213, vol. 91, No. 12.

McCormick, S. et al. "Leaf disc transformation of cultivated tomato (*L. esculentum*) using *Agrobacterium tumefaciens" Plant Cell Reports,* 1986, pp. 81-84, vol. 5.

Navas-Castillo, J. et al. Natural recombination between *Tomato yellow leaf curl virus*-Is and *Tomato leaf curl virus, Journal of General Virology,* 2000, pp. 2797-2801, vol. 81.

Navot, N. et al. "Tomato Yellow Leaf Curl Virus: A Whitefly—Transmitted Geminvirus with a Single Genomic Component" *Virology,* 1991, pp. 151-161, vol. 185.

Noris, E. et al. "Resistance to Tomato Yellow Leaf Curl Geminivirus in *Nicotiana benthaminana* Plants Transformed with a Truncated Viral C1 Gene" *Virology* 1996, pp. 130-138, vol. 224.

Polston, J. E. et al. "The Emergence of Whitefly-Transmitted Geminiviruses in Tomato in the Western Hemisphere" *Plant Disease,* 1997, pp. 1358-1369, vol. 81, No. 12.

Polston, J. E. et al. "Introduction of Tomato Yellow Leaf Curl Virus in Florida and Implications for the Spread of This and Other Geminiviruses of Tomato" *Plant Disease,* 1999, pp. 984-988, vol. 83, No. 11.

Yin, Q. et al. "Discovery and demonstration of small circular DNA molecules derived from Chinese tomato yellow leaf curl virus" *Chinese Science Bulletin,* Aug. 2000, pp. 1417-1421, vol. 45, No. 15.

Schardl, C. L. et al. "Design and construction of a versatile system for the expression of foreign genes in plants" *Gene,* pp. 1-11, vol. 61.

Stout, J. T. et al. "Engineered *rep* Gene-Mediated Resistance to Tomato Mottle Geminivirus in Tomato" *Phytopathology,* 1997, p. S94, vol. 87.

Wei, C-F. et al. "Isolation and Comparison of Two Molecular Species of the BAL 1 Nuclease from *Alteromonas espejiana* with Distinct Kinetic Properties" *The Journal of Biological Chemistry,* Nov. 25, 1983, pp. 13506-13512, vol. 258, No. 22.

Williams, L. et al. "Whitefly Control in Arizona: Development of a Resistance Management Program for Imidacloprid" Cotton Insect Research and Control Conference, Beltwide Cotton Conferences, 1996, pp. 752-755.

Zuo, J. et al. Marker-free transformation: increasing transformation frequency by the use of regeneration-promoting genes *Current Opinion in Biotechnology/Plant biotechnology,* 2002, pp. 173-180, vol. 13.

Jan, F-J. et al. "A single chimeric transgene derived from two distinct viruses confers multi-virus resistance in transgenic plants through homology-dependent gene silencing" *Journal of General Virology,* 2000, pp. 2103-2109, vol. 81.

Antignus, Y. et al. Complete Nucleotide Sequence of an Infectious Clone of a Mild Isolate of Tomato Yellow Leaf Curl Virus (TYLCV), *Phytopathology,* 1994, pp. 707-712, vol. 84, No. 7.

Laufs, J. et al. "Geminivirus replication: Genetic and biochemical characterization of Rep protein function, a review" *Biochimi,* 1995, pp. 765-773, vol. 185.

Kheyr-Pour, A. et al. "Tomato yellow leaf curl virus from Sardinia is a whitefly-transmitted monopartite geminivirus" *Nucleic Acids Research,* 1991, pp. 6763-6769, vol. 19, No. 24.

Jupin, I. et al. "DNA replication specificity of TYLCV geminivirus is medicated by the amino-terminal 116 amino acids of the Rep protein" *FEBS Letters,* 1995, pp. 116-120, vol. 362.

Desbiez, C. et al. "Rep protein of tomato yellow leaf curl geminivirus has an ATPase activity required for viral DNA replication" *Proc. Natl. Acad. Sci. USA,* Jun. 1995, pp. 5640-5644, vol. 92.

Day, A.G. et al. "Expression of an antisense viral gene in transgenic tobacco confers resistance to the DNA virus tomato golden mosaic virus" *Proc Natl. Acad. Sci. USA,* Aug. 1991, pp. 6721-6725, vol. 88.

* cited by examiner

GAATTCGCCCGGGGATCTCCTTTGCCCCAGAGATCACAATGGACGACTTCCTATATCT
CTACGATCTAGTCAGGAAGTTCGACGGAGAAGGTGACGATACCATGTTCACCACTG
ATAATGAGAAGATTAGCCTTTTCAATTTCAGAAAGAATCCTAACCCACAGATGGTTA
GAGACGCTTACGCAGCAGGTCTCATCAAGACGATCTACCCGAGCAATAATCTCCAG
GAGATCAAATACCTTCCCAAGAAGGTTAAAGATGCAGTCAAAAGATTCAGGACTAA
CTGCATCAAGAACACAGAGAAAGATATATTTCTCAAGATCAGAAGTACTATTCCAGT
ATGGACGATTCAAGGCTTGCTTCACAAACCAAGGCAAGTAATAGAGATTGGAGTCT
CTAAAAAGGTAGTTCCCACTGAATCAAAGGCCATGGAGTCAAAGATTCAAATAGAG
GACCTAACAGAACTCGCCGTAAAGACTGGCGAACAGTTCATACAGAGTCTCTTACG
ACTCAATGACAAGAAGAAAATCTTCGTC{*AACATGGTGGAGCACGACACGCTTGTCT*
*ACCTCCAAAAATATCAAAGATACAGTCTCAGAAGACCAAAGGGAATTGAGACTTTT*
*CAACAAAGGGTAATATCCGGAAACCTCCTCGGATTCCATTGCCCAGCTATCTGTCAC*
*TTTATTGTGAAGATAGTGGAAAAGGAAGGTGGCTCCTACAAATGCCATCATTGCGAT*
*AAAGGAAAGGCCATCGTTGAAGATGCCTCTGCCGACAGTGGTCCCAAAGATGGACC*
*CCCACCCACGAGGAGCATCGTGGAAAAAGAAGACGTTCCAACCACGTCTTCAAAGC*
*AAGTGGATTGATGTGAT*}AACATGGTGGAGCACGACACGCTTGTCTACCTCCAAAAA
TATCAAAGATACAGTCTCAGAAGACCAAAGGGAATTGAGACTTTTCAACAAAGGGT
AATATCCGGAAACCTCCTCGGATTCCATTGCCCAGCTATCTGTCACTTTATTGTGAAG
ATAGTGGAAAAGGAAGGTGGCTCCTACAAATGCCATCATTGCGATAAAGGAAAGGC
CATCGTTGAAGATGCCTCTGCCGACAGTGGTCCCAAAGATGGACCCCCACCCACGAG
GAGCATCGTGGAAAAAGAAGACGTTCCAACCACGTCTTCAAAGCAAGTGGATTGA
GTGATATCTCCACTGACGTAAGGGATGACGCACAATCCCACTATCCTTCGCAAGACC

FIG. 3A

CTTCCTCTATATAAGGAAGTTCATTTCATTTGGAGAGGACACGCTGAAATCACCAGT
CTCTCTCTAAGCTTGGATCCTCGAGCTGCAGGAGCTCGAATTGATCCTCTAG
AGCTTTCGTTCGTATCATCGGTTTCGACAACGTTCGTCAAGTTCAATGCATCAGTTTC
ATTGCGCACACACCAGAATCCTACTGAGTTCGAGTATTATGGCATTGGGAAAACTGT
TTTTCTTGTACCATTTGTTGTGCTTGTAATTTACTGTGTTTTTTATTCGGTTTTCGCTATC
GAACTGTGAAATGGAAATGGATGGAGAAGAGTTAATGAATGATATGGTCCTTTTGTT
CATTCTCAAATTAATATTATTTGTTTTTTCTCTTATTTGTTGTGTGTTGAATTTGAAATT
ATAAGAGATATGCAAACATTTTGTTTTGAGTAAAAATGTGTCAAATCGTGGCCTCTA
ATGACCGAAGTTAATATGAGGAGTAAAACACTTGTAGTTGTACCATTATGCTTATTC
ACTAGGCAACAAATATATTTTCAGACCTAGAAAAGCTGCAAATGTTACTGAATACAA
GTATGTCCTCTTGTGTTTTAGACATTTATGAACTTTCCTTTATGTAATTTTCCAGAATCC
TTGTCAGATTCTAATCATTGCTTTATAATTATAGTTATACTCATGGATTTGTAGTTGAG
TATGAAAATATTTTTTAATGCATTTTATGACTTGCCAATTGATTGACAACATGCATCA
ATCGAT

FIG. 3B

FIG. 4
FIG. 5A
FIG. 5B
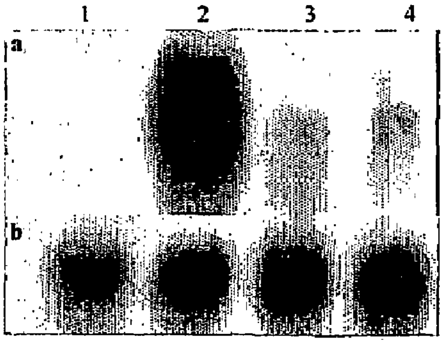

SEQUENCE LISTING

```
<160> NUMBER OF SEQ ID NOS: 8

<210> SEQ ID NO 1
<211> LENGTH: 26
<212> TYPE: DNA
<213> ORGANISM: Tomato yellow leaf curl virus

<400> SEQUENCE: 1

ccaagcttag ccattaggtg tccaag                                          26


<210> SEQ ID NO 2
<211> LENGTH: 27
<212> TYPE: DNA
<213> ORGANISM: Tomato yellow leaf curl virus

<400> SEQUENCE: 2

ctctcgaggg atttactgcc tgaattg                                         27


<210> SEQ ID NO 3
<211> LENGTH: 142
<212> TYPE: PRT
<213> ORGANISM: Tomato yellow leaf curl virus

<400> SEQUENCE: 3

Met Pro Arg Leu Phe Lys Ile Tyr Ala Lys Asn Tyr Phe Leu Thr Tyr
1               5                   10                  15

Pro Asn Cys Ser Leu Ser Lys Glu Glu Ala Leu Ser Gln Leu Lys Lys
            20                  25                  30

Leu Glu Thr Pro Thr Asn Lys Lys Tyr Ile Lys Val Cys Lys Glu Leu
        35                  40                  45

His Glu Asn Gly Glu Pro His Leu His Val Leu Ile Gln Phe Glu Gly
    50                  55                  60

Lys Tyr Gln Cys Lys Asn Gln Arg Phe Phe Asp Leu Val Ser Pro Asn
65                  70                  75                  80

Arg Ser Ala His Phe His Pro Asn Ile Gln Ala Ala Lys Ser Ser Thr
                85                  90                  95
```

-continued

```
Asp Val Lys Thr Tyr Val Glu Lys Asp Gly Asn Phe Ile Asp Phe Gly
            100                 105                 110

Val Ser Gln Ile Asp Gly Arg Ser Ala Arg Gly Gly Gln Gln Ser Ala
        115                 120                 125

Asn Asp Ala Tyr Ala Glu Ala Leu Asn Ser Gly Ser Lys Ser
    130                 135                 140


<210> SEQ ID NO 4
<211> LENGTH: 508
<212> TYPE: DNA
<213> ORGANISM: Tomato yellow leaf curl virus

<400> SEQUENCE: 4

tagccattag gtgtccaagt ataagtaaga caccgataca ccgattgcca tagagctttg      60

agggacaccg attcatttca acatgcctcg tttatttaaa atatatgcca aaaattattt     120

cctaacatat cccaattgtt ctctctctaa agaggaagca ctttcccaat taaaaaaact     180

agaaacccca acaaataaaa aatacatcaa agtttgcaaa gaactccacg agaatgggga     240

accacatctc catgtgctta tccaattcga aggcaaatac caatgtaaga accaacggtt     300

cttcgacttg gtatccccaa acaggtcagc acatttccat ccgaacattc aggcagctaa     360

gagctcaaca gatgtcaaga cctacgtgga gaaagacgga aacttcattg attttggagt     420

ttcccaaatc gatggcagat cagctagagg aggtcagcaa tctgccaacg acgcatatgc     480

cgaagcactc aattcaggca gtaaatcc                                         508


<210> SEQ ID NO 5
<211> LENGTH: 508
<212> TYPE: DNA
<213> ORGANISM: artificial sequence
<220> FEATURE:
<223> OTHER INFORMATION: Antisense sequence to tomato yellow leaf curl
      virus

<400> SEQUENCE: 5

ggatttactg cctgaattga gtgcttcggc atatgcgtcg ttggcagatt gctgacctcc      60

tctagctgat ctgccatcga tttgggaaac tccaaaatca atgaagtttc cgtctttctc     120

cacgtaggtc ttgacatctg ttgagctctt agctgcctga atgttcggat ggaaatgtgc     180

tgacctgttt ggggatacca agtcgaagaa ccgttggttc ttacattggt atttgccttc     240

gaattggata agcacatgga gatgtggttc cccattctcg tggagttctt tgcaaacttt     300

gatgtatttt ttatttgttg gggtttctag ttttttttaat tgggaaagtg cttcctcttt     360

agagagagaa caattgggat atgttaggaa ataatttttg gcatatattt taaataaacg     420

aggcatgttg aaatgaatcg gtgtccctca aagctctatg gcaatcggtg tatcggtgtc     480

ttacttatac ttggacacct aatggcta                                         508


<210> SEQ ID NO 6
<211> LENGTH: 508
<212> TYPE: DNA
<213> ORGANISM: Tomato yellow leaf curl virus

<400> SEQUENCE: 6

tagccattag gtgtcgaggt attagtaaga caccgataca ccgattgcca tagagctttg      60

agggacaccg attcatttca acatgcctcg tttatttaaa atatatgcca agaattattt     120

cctaacatat cccaattgtt ctctctctaa agaggaagca ctttcccaat taaaaaacat     180

agaaacccca acaaataaaa aatacatcaa agtttgcaga gaattccacg agaatgggga     240
```

-continued

```
accacatctc catgtgctta tccaattcga aggcaaatac caatgtaaga accaacggtt    300

cttcgacctg gtatccccaa acaggtcagc acatttccat ccaaacattc aggcagctaa    360

gagctcaaca gatgtcaaga cctacgtgga gaaagacgga gacttcattg attttggagt    420

tttccaaatc gatggcagat cagctagagg aggtcagcaa tctgccaacg acgcatacgc    480

cggagcactc aattcaggca gtaaatcc                                       508
```

<210> SEQ ID NO 7
<211> LENGTH: 691
<212> TYPE: DNA
<213> ORGANISM: artificial sequence
<220> FEATURE:
<223> OTHER INFORMATION: Antisense sequence to tomato yellow leaf curl virus

<400> SEQUENCE: 7

```
agagcgaccc actcttcaag ttcatctgga acttgattaa aagaagaaga aagaaatgga     60

gaaacataaa cttctaaagg aggactaaaa atcctatcta aatttgaatt taaattatga    120

aattgtaaaa tatagtcctt tggggccttt tcttttaata tattgagggc ctcggattta    180

ctgcctgaat tgagtgctcc ggcgtatgcg tcgttggcag attgctgacc tcctctagct    240

gatctgccat cgatttggaa aactccaaaa tcaatgaagt ctccgtcttt ctccacgtag    300

gtcttgacat ctgttgagct cttagctgcc tgaatgtttg gatggaaatg tgctgacctg    360

tttggggata ccaggtcgaa gaaccgttgg ttcttacatt ggtatttgcc ttcgaattgg    420

ataagcacat ggagatgtgg ttccccattc tcgtggaatt ctctgcaaac tttgatgtat    480

tttttatttg ttggggtttc tatgtttttt aattgggaaa gtgcttcctc tttagagaga    540

gaacaattgg gatatgttag gaaataattc ttggcatata ttttaaataa acgaggcatg    600

ttgaaatgaa tcggtgtccc tcaaagctct atggcaatcg gtgtatcggt gtcttactaa    660

tacctggaca cctaatggct atttctctag a                                   691
```

<210> SEQ ID NO 8
<211> LENGTH: 1998
<212> TYPE: DNA
<213> ORGANISM: artificial sequence
<220> FEATURE:
<223> OTHER INFORMATION: Expression vector

<400> SEQUENCE: 8

```
gaattcgccc ggggatctcc tttgccccag agatcacaat ggacgacttc ctatatctct     60

acgatctagt caggaagttc gacggagaag gtgacgatac catgttcacc actgataatg    120

agaagattag ccttttcaat ttcagaaaga atcctaaccc acagatggtt agagacgctt    180

acgcagcagg tctcatcaag acgatctacc cgagcaataa tctccaggag atcaaatacc    240

ttcccaagaa ggttaaagat gcagtcaaaa gattcaggac taactgcatc aagaacacag    300

agaaagatat atttctcaag atcagaagta ctattccagt atggacgatt caaggcttgc    360

ttcacaaacc aaggcaagta atagagattg gagtctctaa aaaggtagtt cccactgaat    420

caaaggccat ggagtcaaag attcaaatag aggacctaac agaactcgcc gtaaagactg    480

gcgaacagtt catacagagt ctcttacgac tcaatgacaa gaagaaaatc ttcgtcaaca    540

tggtggagca cgacacgctt gtctacctcc aaaaatatca aagatacagt ctcagaagac    600

caaagggaat tgagactttt caacaaaggg taatatccgg aaacctcctc ggattccatt    660

gcccagctat ctgtcacttt attgtgaaga tagtggaaaa ggaaggtggc tcctacaaat    720
```

-continued

```
gccatcattg cgataaagga aaggccatcg ttgaagatgc ctctgccgac agtggtccca    780
aagatggacc cccacccacg aggagcatcg tggaaaaaga agacgttcca accacgtctt    840
caaagcaagt ggattgatgt gataacatgg tggagcacga cacgcttgtc tacctccaaa    900
aatatcaaag atacagtctc agaagaccaa agggaattga gacttttcaa caaagggtaa    960
tatccggaaa cctcctcgga ttccattgcc cagctatctg tcactttatt gtgaagatag   1020
tggaaaagga aggtggctcc tacaaatgcc atcattgcga taaaggaaag gccatcgttg   1080
aagatgcctc tgccgacagt ggtcccaaag atggaccccc acccacgagg agcatcgtgg   1140
aaaaagaaga cgttccaacc acgtcttcaa agcaagtgga ttgatgtgat atctccactg   1200
acgtaaggga tgacgcacaa tcccactatc cttcgcaaga cccttcctct atataaggaa   1260
gttcatttca tttggagagg acacgctgaa atcaccagtc tctctctaag cttggatcct   1320
cgagctgcag gagctcgaat tgatcctcta gagctttcgt tcgtatcatc ggtttcgaca   1380
acgttcgtca agttcaatgc atcagtttca ttgcgcacac accagaatcc tactgagttc   1440
gagtattatg gcattgggaa aactgttttt cttgtaccat ttgttgtgct tgtaatttac   1500
tgtgtttttt attcggtttt cgctatcgaa ctgtgaaatg gaaatggatg gagaagagtt   1560
aatgaatgat atggtccttt tgttcattct caaattaata ttatttgttt tttctcttat   1620
ttgttgtgtg ttgaatttga aattataaga gatatgcaaa cattttgttt tgagtaaaaa   1680
tgtgtcaaat cgtggcctct aatgaccgaa gttaatatga ggagtaaaac acttgtagtt   1740
gtaccattat gcttattcac taggcaacaa atatattttc agacctagaa aagctgcaaa   1800
tgttactgaa tacaagtatg tcctcttgtg ttttagacat ttatgaactt tcctttatgt   1860
aattttccag aatccttgtc agattctaat cattgcttta taattatagt tatactcatg   1920
gatttgtagt tgagtatgaa aatatttttt aatgcatttt atgacttgcc aattgattga   1980
caacatgcat caatcgat                                                 1998
```

MATERIALS AND METHODS FOR PRODUCING TOMATO YELLOW LEAF CURL VIRUS RESISTANCE IN PLANTS

CROSS-REFERENCE TO RELATED APPLICATION

This application is a U.S. national stage application filed from international patent application No. PCT/US02/14481, filed May 7, 2002, which claims the benefit of U.S. Provisional application Ser. No. 60/289,315, filed May 7, 2001, now abandoned.

The subject invention was made with government support under a research project supported by the USDA Grant Nos. 99343628423, 98341356784 and 99341358478. The government has certain rights in this invention.

BACKGROUND OF THE INVENTION

Whitefly-transmitted geminiviruses have become a major limiting factor in tomato production in Florida, the Caribbean and much of Latin America. This group of viruses is currently expanding in the Western Hemisphere, and the number of characterized geminiviruses which infect tomato in this region has increased from three to more than 17 over the last 15 years (Polston and Anderson, 1997). This expansion is continuing and reports of new epidemics are appearing almost monthly. Whitefly-transmitted viruses appear alone and in mixed infections with other geminiviruses and other viruses. Whitefly-transmitted geminiviruses are reducing tomato yields in many countries, and total crop losses are not uncommon (Polston and Anderson, 1997). In Florida, tomato production has suffered significant losses (estimated at $125 million in 1990-91) due to Tomato mottle virus (ToMoV) infection, which first appeared in 1989 and to Tomato yellow leaf curl virus (TYLCV), which has caused crop failures and increases in production costs due to increases in pesticide use.

The family Geminiviridae is divided into three genera, of which the genus, *Begomovirus,* contains the whitefly-transmitted geminiviruses. There are two major divisions within the genus *Begomovirus,* those with monopartite genomes and those with bipartite genomes. The taxonomy of Begomoviruses is in a state of confusion, due to the naming of viruses based on disease symptoms before any sequence analysis has been performed. Many of these viruses cause similar symptoms in the same host, which has resulted in very different viruses having the same or related name in the literature. This is particularly true for tomato yellow leaf curl virus (TYLCV). There are eight separate and unique Begomoviruses named TYLCV. Recent suggestions to resolve this confusion have been published, though none have been adopted by all virologists, with the result that different viruses are referred to in a number of different ways. Using the scheme suggested by Fauquet and Mayo (1999), the eight viruses are identified based on the country from where the virus was first described: from China (TYLCV-Ch), from Israel (also the first one to be described) (TYLCV-Is), from Nigeria (TYLCV-Ng), from Sardinia (TYLCV-Sar), from southern Saudi Arabia (TYLCV-SSA), from Tanzania (TYLCV-Tz), from Thailand (TYLCV-Th), and from Yemen (TYLCV-Ye). Thus, while each of these viruses is named TYLCV, each of these viruses have unique sequences with less than 90% sequence homology over the genome.

The geminivirus referred to as tomato yellow leaf curl virus-Israel (TYLCV-Is), which caused extensive losses to tomato production in the Dominican Republic (reviewed by Polston and Anderson, 1997), was found in Florida in 1997 (Polston et al., 1999). TYLCV-Is infection of tomato is a serious problem in the United States Florida, Georgia, Louisiana, and Mississippi), the Caribbean (The Bahamas, Cuba, Dominican Republic, Puerto Rico, and Jamaica), Mexico, Japan, Europe, and the Mediterranean (Canary Islands, Egypt, Israel, Cyprus, Italy, Spain, Portugal and Morocco). Incidences of TYLCV-Is are increasing and economic losses have been experienced as recently as fall of 1998. TYLCV-Is virus is widespread in Florida, is likely to increase over the next few years and will become a major constraint to tomato production in Florida. Currently, there are few commercial tomato cultivars on the market with resistance to infection by TYLCV-Is. The resistance is categorized as tolerance, since infected plants show no to slight symptoms and produce yields that are relatively unaffected by infection; however, the virus can still be detected in inoculated plants and these plants can serve as sources of inoculum for susceptible cultivars and crops (Lapidot et al., 2001).

Geminiviruses are very difficult to economically manage in fresh market tomatoes, and practically impossible to manage in processing tomatoes. At this time, geminiviruses are managed primarily through the use of a single insecticide, imidacloprid (Bayer Agricultural Products, Kansas City, Mo.), to reduce the population of the whitefly vector. Tolerance to this insecticide has already been reported (Cahill et al., 1996; Williams et al., 1996). It may be only a matter of time before imidacloprid loses efficacy in the United States and other locations. The average Florida tomato grower spent approximately $250/acre for insecticides to control ToMoV in 1994 through 1997. These costs have increased significantly as U.S. growers' struggle to manage TYLCV-Is. In Caribbean countries geminiviruses have caused many small and medium size tomato growers to go out of business due the increases in costs of production and crop losses. In Israel, where imidacloprid resistance is present, TYLCV-Is is managed by pesticide use plus exclusion; tomatoes are produced in planthouses enclosed in whitefly-proof screening material or in screened tunnels in the field. The use of these methods is expensive and is often not an economically or horticulturally realistic alternative. The least expensive and most practical control of whitefly-transmitted geminiviruses is the use of resistant cultivars. At this time there are no commercially available resistant tomato cultivars for the geminiviruses native to the Western Hemisphere. As noted above, there are only two cultivars with tolerance to TYLCV-Is that are suitable for production in the U.S. This resistance is derived from wild species of *Lycopersicon,* probably *L. peruvianum* and *L. pimpinellifolium.*

There are a few reports suggesting that the gene encoding the Begomovirus replication associated protein (Rep) might be used for resistance to viral infection. There has been a report that a modified ToMoV Rep mutated in an NTP-binding motif was transformed into tomato plants and demonstrated to interfere with viral replication (Stout et al., 1997). Hanson et al. (1999) analyzed phenotypes of BGYMV (bean golden yellow mosaic virus) with mutations in an NTP-binding motif of the Rep gene, and demonstrated that the NTP-binding domain is required for replication. They proposed that mutations in this motif might serve in a trans-dominant negative interference scheme for pathogen-derived resistance (also known as "dominant negative mutations"). Resistance to African cassava mosaic geminivirus (ACMV) in *Nicotiana benthamiana* plants was developed by transformation with ACMV Rep (Hong and Stanley, 1996).

Some viral resistance has been reported using the Rep gene of the geminivirus TYLCV from Sardinia (TYLCV-Sar). However, TYLCV-Sar is a distinct virus, only distantly related to TYLCV-Is and shows significant differences in the genomic sequence (<80% homology). Noris et al (1996) found TYLCV-Sar resistance in *N. benthamiana* plants using the TYLCV-Sar Cl gene that encodes a protein with a truncated C-terminal (210 amino acids). However, resistance was overcome with time. Brunetti et al. (1997) transformed tomatoes with the same construct and found that high accumulation of the truncated Rep protein was required for resistance, that high accumulation resulted in a "curled" phenotype, and that the resistance did not extend to an unrelated geminivirus. Transgenic *Nicotiana benthamiana* plants expressing antisense RNA to the Rep gene have been observed with resistance to TYLCV-Sar infection (Bendahmane and Gronenborn, 1997). The plants transformed according to the methods of the subject invention have a normal phenotype and are expected to be high yielding as well.

The present invention overcomes the expensive, time consuming, and limited options in the traditional plant breeding programs applied to generating virus resistant tomato cultivars.

BRIEF SUMMARY OF THE INVENTION

The subject invention concerns materials and methods for providing genetically-engineered resistance to tomato yellow leaf curl geminivirus, such as TYLCV-Israel (TYLCV-Is), in plants while maintaining acceptable phenotypic characteristics of the plant. In exemplified embodiments, the subject invention provides TYLCV-Is resistance in tomato and tobacco. Specifically, resistance is provided by transforming a plant with a truncated version of the replication associated protein (Rep) gene of TYLCV. Exemplified herein is the use of a truncated Rep gene from TYLCV-Is (Florida isolate). The full length Rep gene of TYLCV-Is encodes a virus replication related protein of approximately 357 amino acids. In an exemplified embodiment, the Rep gene used in the present methods was truncated at the 3' end, leaving 508 nucleotides (nt) at the 5' terminus which comprised an 82 nt intergenic sequence and a 426 nt sequence that encodes a Rep protein fragment (N-terminus) of 142 amino acids. In another embodiment, a polynucleotide that is antisense to a truncated Rep gene of the present invention is used to provide resistance to infection. The present invention demonstrates the application of genetic engineering in the development of TYLCV-Is resistance in a tomato breeding line suitable for use in a hybrid for tomato production in Florida.

BRIEF DESCRIPTION OF THE DRAWINGS

FIGS. 3A-3B show the sequence of the expression cassette in PKYLX71:35S2 (SEQ ID NO. 8). The region duplicated to create the 35S2 promoter is bounded by brackets and italicized (this is the first of the two repeats), and the transcription start site, multiple cloning sites and the principal 3' end in the rbcS-E9 3' region are set off in bold type. The expression cassette is bounded by Eco RI and Cla I sites.

FIG. 4 shows a tomato plant (in back) transformed with the truncated Rep gene showing resistance to TYLCV. Non-transformed tomato (in front) shows TYLCV disease symptoms. The test was conducted in the field at Bradenton, Fla. during the fall of 2000. All test plants were exposed to viruliferous whiteflies prior to transplanting in the field.

FIGS. 5A-5B show a Northern blot analyses of total RNA extracted from transgenic 2/5 Rep tobacco plants and a non-transformed control. FIG. 5A, lane 1 shows a non-transformed plant; lane 2 shows non-inoculated 2/5 Rep plant; and lanes 3 and 4 show C1T1 plants inoculated with TYLCV. FIG. 5B, shows the same blot probed with 18S rRNA gene to confirm equal loading of RNA in lanes.

BRIEF DESCRIPTION OF SEQUENCES

Figure 1:
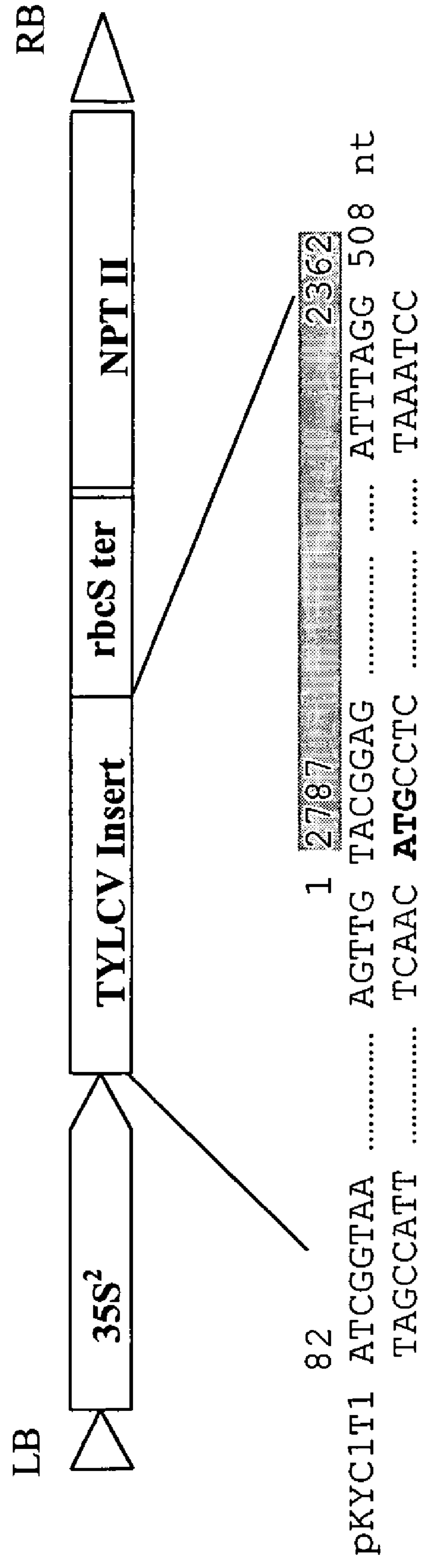
FIG. 1 shows a representation of the binary transformation vector with the truncated TYLCV Rep gene. The upper sequence corresponds to SEQ ID NO: 5 and the lower sequence corresponds to SEQ ID NO: 4.

SEQ ID NO. 1 is a oligonucleotide used for primary PCR amplification of a fragment of the Rep gene according to the present invention.

SEQ ID NO. 2 is a oligonucleotide used for primary PCR amplification of a fragment of the Rep gene according to the present invention.

SEQ ID NO. 3 shows the amino acid sequence of a truncated Rep protein according to the present invention.

SEQ ID NO. 4 shows the nucleotide sequence of a truncated TYLCV-Is Rep gene according to the present invention that encodes the amino acid sequence of SEQ ID NO. 3 and that includes an 81 nucleotide intergenic region.

SEQ ID NO. 5 shows a nucleotide sequence that is the antisense of a truncated TYLCV-Is Rep gene of SEQ ID NO. 4 according to the present invention, including the 81 nucleotide intergenic region.

SEQ ID NO. 6 shows the nucleotide sequence of a truncated TYLCV-Is (Florida isolate) Rep gene according to the present invention that encodes the amino acid sequence of SEQ ID NO. 3 and that includes an 82 nucleotide intergenic region.

SEQ ID NO. 7 shows a nucleotide sequence that is the antisense of a truncated TYLCV-Is (Florida isolate) Rep gene of SEQ ID NO. 6 according to the present invention, including the 82 nucleotide intergenic region.

SEQ ID NO. 8 shows the nucleotide sequence of the expression cassette in PKYLX71:35S2 according to the present invention.

DETAILED DISCLOSURE OF THE INVENTION

The present invention provides a means for producing virus resistance in tomato and other crops that are susceptible to infection by TYLCV-Is (tomato yellow leaf curl virus-Israel). In exemplified embodiments, plants having resistance to TYLCV-Is were produced. The transformed and transgenic plants produced according to the present invention exhibit normal phenotypic qualities such that the plants and their produced crop are acceptable for commercial use. Development of TYLCV-Is resistance through conventional breeding has been slow (more than 10 years for traditional breeding versus 3-5 years for genetic engineered technology), usually depends upon multiple genes, and often is compromised by linkages of resistance genes to undesirable horticultural characteristics. The present invention greatly simplifies production of TYLCV-Is resistant plants and the introduction of a TYLCV-Is resistance gene into desirable tomato lines.

The subject invention concerns methods for providing resistance to infection by a tomato yellow leaf curl virus (TYLCV) in a plant or plant tissue by transforming a plant or plant tissue with a polynucleotide selected from i) a polynucleotide comprising a fragment of a TYLCV Rep gene, wherein the fragment of the Rep gene consists of all or a portion of the 5' intergenic region of a Rep gene and about 400 to 500 nucleotides of the 5' coding sequence of a Rep gene; ii) a polynucleotide comprising a sequence that is antisense to the fragment of the TYLCV Rep gene, and iii) a polynucleotide comprising a sequence that hybridizes under stringent conditions with the fragment of the TYLCV Rep gene or a sequence that is antisense to the fragment of the TYLCV Rep gene. Resistance to TYLCV selected from TYLCV-China, TYLCV-Israel, TYLCV-Nigeria, TYLCV-Sardinia, TYLCV-southern Saudi Arabia, TYLCV-Tanzania, TYLCV-Thailand, and TYLCV-Yemen is specifically contemplated by the subject method. Plants that can be provided with resistance to TYLCV infection include tomato, tobacco, statice, petunia, lisianthus, tomatillo, and other plants susceptible to infection by TYLCV.

In an exemplified embodiment, the subject invention provides plants having genetically-engineered resistance to TYLCV using a polynucleotide which encodes a truncated version of the replication associated (Rep) protein of TYLCV and includes a Rep intergenic region. Preferably, the truncated Rep gene is derived from TYLCV-Is or a Florida isolate of TYLCV. In one embodiment, the Rep gene of the Florida isolate of TYLCV-Is, which encodes a virus replication related protein of 357 amino acids, was truncated at the 3' end, leaving 508 nucleotides (nt) (SEQ ID NO. 6) at the 5' terminus which comprises 82 nucleotides of the Rep intergenic region and 426 nucleotides that encode a Rep protein fragment of 142 amino acids (SEQ ID NO. 3). The exemplified Rep gene fragment represents a small part (approximately 40%) of the full-length Rep gene of the virus. In another embodiment, a polynucleotide that is antisense to a truncated Rep gene of the present invention is used to provide resistance to infection. In one embodiment, the antisense polynucleotide has a sequence shown in any of SEQ ID NOS. 5 or 7. Polynucleotide sequences that hybridize with or that have 50% or more sequence identity with the truncated Rep gene sequences or antisense sequences are also contemplated within the scope of the invention. Also contemplated within the scope of the invention are fragments of a truncated Rep gene and fragments of sequences antisense to a truncated Rep gene of the present invention, including fragments of a polynucleotide having the sequence of any of SEQ ID NOS. 4-7, and fragments of the hybridizing sequences or sequences with sequence identity, so long as the fragment when expressed in a plant confers resistance to TYLCV on that plant. Methods for generating fragments of a polynucleotide sequence are well known in the art (see, for example, Wei et al., 1983).

The truncated Rep genes of the present invention can be introduced directly into plants, such as tomato, by *Agrobacterium*-mediated transformation or by gene transfer through conventional breeding from the transformed breeding line and, thus, can be used to protect plants from TYLCV-Is infection. Thus, the subject invention also concerns new breeding lines of plants, including tomato, with high levels of resistance to TYLCV, such as TYLCV-Is. By using new breeding lines comprising a modified Rep gene of the present invention, breeders can generate new cultivars of tomato that are resistant to virus without sacrificing other desired agronomic and horticulture features.

In a preferred embodiment of the invention, a virus-resistant transgenic plant line prepared according to the methods described herein is crossed with a transgenic plant line that is resistant to the same virus and derived from a different transformation event to produce hybrids that exhibit increased virus resistance over the parent lines. These hybrid plants are within the scope of the present invention.

Because of the high levels of resistance conferred by the methods of the present invention, application of new tomato cultivars generated from the breeding lines containing a truncated Rep gene of the present invention can greatly reduce the production loss caused by virus infection which can decrease fruit yield by up to 100%. Moreover, the use of truncated Rep gene-containing cultivars of the present invention can significantly reduce the dependence on pesticides to control whitefly that is the vector of TYLCV-Is and other geminiviruses, and consequently reduce tomato production costs and environmental contamination by pesticides. At this time, TYLCV-Is management is heavily dependent upon a single insecticide that is translocated systemically in plants. Once the whiteflies become resistant to this insecticide, management of TYLCV-Is will be nearly impossible. Therefore, application of this invention can benefit tomato growers and society as a whole by increasing productivity and reducing production costs and environment contamination.

Preferably, truncated Rep transgenes of the present invention already have markers to assist in breeding efforts (marker-assisted selection). In contrast to the results obtained by Brunetti et al. (1997), the use of Rep transgenes of the invention, to date, have not shown any adverse affects on the phenotype of virus-resistant but non-inoculated transformed plants. Resistant plants showed no evidence of virus replication 30 to 60 days after inoculation, as established by nucleic acid spot hybridization and PCR. A truncated Rep gene of the present invention can be readily moved either through transformation or through conventional breeding techniques into new horticultural backgrounds that will provide superior horticultural traits for production. In addition, use of the truncated Rep gene of the present invention in plants does not interfere with fruit size, as do the currently available resistance genes.

The subject invention also concerns polynucleotide molecules selected from i) a polynucleotide comprising a fragment of a TYLCV Rep gene, wherein the fragment of the Rep gene consists of all or a portion of the 5' intergenic region of a Rep gene and about 400 to 500 nucleotides of the 5' coding sequence of a Rep gene; ii) a polynucleotide comprising a sequence that is antisense to the fragment of the TYLCV Rep gene, and iii) a polynucleotide comprising a sequence that hybridizes under stringent conditions with the fragment of the TYLCV Rep gene or a sequence that is antisense to the fragment of the TYLCV Rep gene, such that when the polynucleotide is incorporated into the genome of a plant, the plant is resistant to infection by plant viruses but without negatively impacting the phenotypic characteristics of the plant. Polynucleotide sequences that hybridize with or that have 50% or more sequence identity with the truncated Rep gene sequences or antisense sequences are also contemplated within the scope of the invention. Also contemplated within the scope of the invention are fragments of a truncated Rep gene and fragments of sequences antisense to a truncated Rep gene of the present invention, including fragments of a polynucleotide having the sequence of any of SEQ ID NOS. 4-7, and fragments of the hybridizing sequences or sequences with sequence identity, so long as the fragment when expressed in a plant confers resistance to TYLCV on that plant.

In addition, because of the redundancy of the genetic code, polynucleotides of the invention can have numerous, different sequences which encode a truncated Rep polypeptide. It is well within the skill of a person trained in the art to create alternative polynucleotide sequences encoding the same, or essentially the same, truncated Rep polypeptide. These variant or alternative polynucleotide sequences are within the scope of the subject invention. As used herein, references to "essentially the same" sequence refers to sequences which encode amino acid substitutions, deletions, additions, or insertions in a truncated Rep protein which do not materially alter the ability of the polynucleotide to confer resistance to virus infection when inserted into a plant genome. Polynucleotides of the present invention encoding conservative substitutions, whereby an amino acid of one class (non-polar, uncharged polar, basic, and acidic) is replaced with another amino acid of the same class, fall within the scope of the subject invention so long as the substitution does not materially alter the ability of the present invention to provide resistance. Also contemplated within the scope of the invention are polynucleotides that are longer or shorter than the exemplified polynucleotide so long as the longer or shorter polynucleotide confers viral resistance on the plant without negatively impacting the phenotypic characteristics of the plant.

The subject invention also concerns recombinant polynucleotide vectors comprising a truncated Rep gene of the present invention which is expressible in a suitable host plant. Suitable vectors may be selected from those known in the art including plasmids, phage DNA, or combinations of plasmids and phage DNA, yeast plasmids, and derivatives and fragments. Polynucleotides of the present invention can be inserted into the multiple cloning site of a vector, such as the commercially available pUC vectors or the pGEM vectors, which allow for the excision of the polynucleotide having restriction termini adapted for insertion into any desirable plant expression or integration vector. Other plant expression vectors can also be used in the present invention. In addition, regulatory sequences such as promoters can be operatively linked to the coding sequences of polynucleotides of the present invention. For example, the 35S or 35S2 promoter of cauliflower mosaic viruses (CaMV) can be used with the subject invention. Plant promoters, such as Ap3 promoter, heat shock 80 promoter, alfalfa histone H3.2 gene promoter (Kelemen et al., 2002), E8 promoter, and the like, can be used in the present invention. Other suitable promoters include octopine synthase promoter and nopaline synthase promoter. The promoter can be a constitutive, tissue-specific, or inducible promoter.

The expression vector can also, optionally, contain a selectable marker gene. In one embodiment, a marker gene provides for antibiotic or herbicide resistance when expressed. Antibiotic resistance markers include, for example, polynucleotide that when expressed provides resistance to G418, hygromycin, bleomycin, kanamycin, gentamicin and the like. Herbicide resistance markers include, for example, a polynucleotide that when expressed provides resistance to glyphosate, sulfonylurea, and the like. In one embodiment, a polynucleotide encoding the enzyme neomycin phosphotransferase type II is incorporated into an expression vector of the invention. This enzyme confers resistance to the antibiotic kanamycin. Cells transformed with a vector of the present invention containing an antibiotic or herbicide resistance marker gene can be identified by their ability to grow in the presence of the antibiotic or herbicide.

The vector can also include a 3' non-translated termination segment operatively linked to the 3' end of the coding sequence of the truncated Rep gene. The 3' termination segment can provide for the addition of a polyadenylation signal to the 3' end of mRNA. Any 3' termination segment suitable for use in plants is within the scope of the invention.

The present invention also concerns cells infected, transformed, or transfected with a polynucleotide comprising a truncated Rep gene of the present invention. Preferably, the truncated Rep gene is derived from TYLCV-Is and comprises a nucleotide sequence coding for a polypeptide having the amino acid sequence shown in SEQ ID NO. 3. In an exemplified embodiment, the polynucleotide comprises a nucleotide sequence shown in SEQ ID NO. 6. In one embodiment, the polynucleotide is incorporated into a suitable vector, and the recombinant vector is used to transform a bacterium or other host which can then be used to introduce the polynucleotide into a plant cell. Suitable hosts that can be infected, transformed, or transfected with a polynucleotide of the invention include gram positive and gram negative bacteria such as *E. coli* and *Bacillus subtilis*. Other suitable hosts include *Agrobacterium* cells, insect cells, plant cells, and yeast cells. *Agrobacterium* containing a polynucleotide of the invention can be used to transform plant cells with the polynucleotide according to standard methods known in the art. For *Agrobacterium* transformation, polynucleotide vectors of the invention can also include T-DNA sequences. Polynucleotides can also be introduced into plant cells by a biolistic method (Carrer, 1995), by electroporation, by direct gene injection, and by other methods known in the art. Plants can also be transformed with polynucleotides of the present invention using marker-free transformation techniques (Zuo et al., 2002).

The subject invention also concerns transformed and transgenic plants and plant tissue, including plant seeds, that comprise a truncated Rep gene of the present invention and that exhibit resistance to infection by plant TYLCV geminiviruses such as TYLCV-Is. In one embodiment, a transformed or transgenic plant of the invention comprises a polynucleotide that comprises a truncated Rep gene of the present invention. In an exemplified embodiment, the truncated Rep gene is derived from TYLCV-Is and comprises a nucleotide sequence coding for a polypeptide having the amino acid sequence shown in SEQ ID NO. 3. In an exemplified embodiment, the polynucleotide comprises a nucleotide sequence shown in SEQ ID NO. 4 or SEQ ID NO. 6. In another embodiment, the plant comprises a polynucleotide comprising an antisense sequence shown in SEQ ID NO. 5 and SEQ ID NO. 7. Transformed and transgenic plants and plant tissue of the invention can be prepared from plants such as tomato (*Lycopersicon esqulentum*), tobacco (*Nicotiana* species), statice (*Limonium sinuatum*), petunia (*Petunia hybrida*), lisianthus (*Eustoma grandiflora*), tomatillo (*Physalis ixocarpa*), pepper, bean, and others that can be or that are susceptible to being infected by TYLCV-Is. The subject invention also concerns progeny of transgenic plants of the invention.

As used herein, the terms "nucleic acid" and "polynucleotide" refer to a deoxyribonucleotide or ribonucleotide polymer in either single- or double-stranded form, and unless otherwise limited, would encompass known analogs of natural nucleotides that can function in a similar manner as naturally-occurring nucleotides. The polynucleotide sequences include both the DNA strand sequence that is transcribed into RNA and the RNA sequence that is translated into protein. The complementary sequence of any nucleic acid or polynucleotide of the present invention is also contemplated within the scope of the invention. The polynucleotide sequences include both full-length sequences that encode the Rep protein of the invention as well as shorter sequences derived from the full-length sequences. It is understood that a particular polynucleotide sequence includes the degenerate codons of the native sequence or sequences which may be introduced to provide codon preference in a specific host cell. Allelic variations of the exemplified sequences also come within the scope of the subject invention.

Polynucleotides and proteins of the subject invention can also be defined in terms of more particular identity and/or similarity ranges with those exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCB/NIH website.

The subject invention also contemplates those polynucleotide molecules having sequences which are sufficiently homologous with the sequences exemplified herein so as to permit hybridization with that sequence under standard stringent conditions and standard methods Maniatis, T. et al., 1982). As used herein, "stringent" conditions for hybridization refers to conditions wherein hybridization is typically carried out overnight at 20-25 C below the melting temperature (Tm) of the DNA hybrid in 6×SSPE, 5× Denhardt's solution, 0.1% SDS, 0.1 mg/ml denatured DNA. The melting temperature is described by the following formula (Beltz, G. A. et al., 1983):

$$Tm=81.5\ C+16.6\ \mathrm{Log}\ [Na+]+0.41(\%\ G+C)-0.61(\%\ \mathrm{formamide})-600/\mathrm{length\ of\ duplex\ in\ base\ pairs}.$$

Washes are typically carried out as follows:

(1) Twice at room temperature for 15 minutes in 1×SSPE, 0.1% SDS (low stringency wash).

(2) Once at Tm-20 C for 15 minutes in 0.2×SSPE, 0.1% SDS (moderate stringency wash).

Thus, specifically contemplated within the scope of the invention are polynucleotide sequences that hybridize under stringent conditions with the sequence of SEQ ID NO. 4, SEQ ID NO. 5, SEQ ID NO. 6, or SEQ ID NO. 7.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Production of Transformed Tomato Plants

Figure 2:
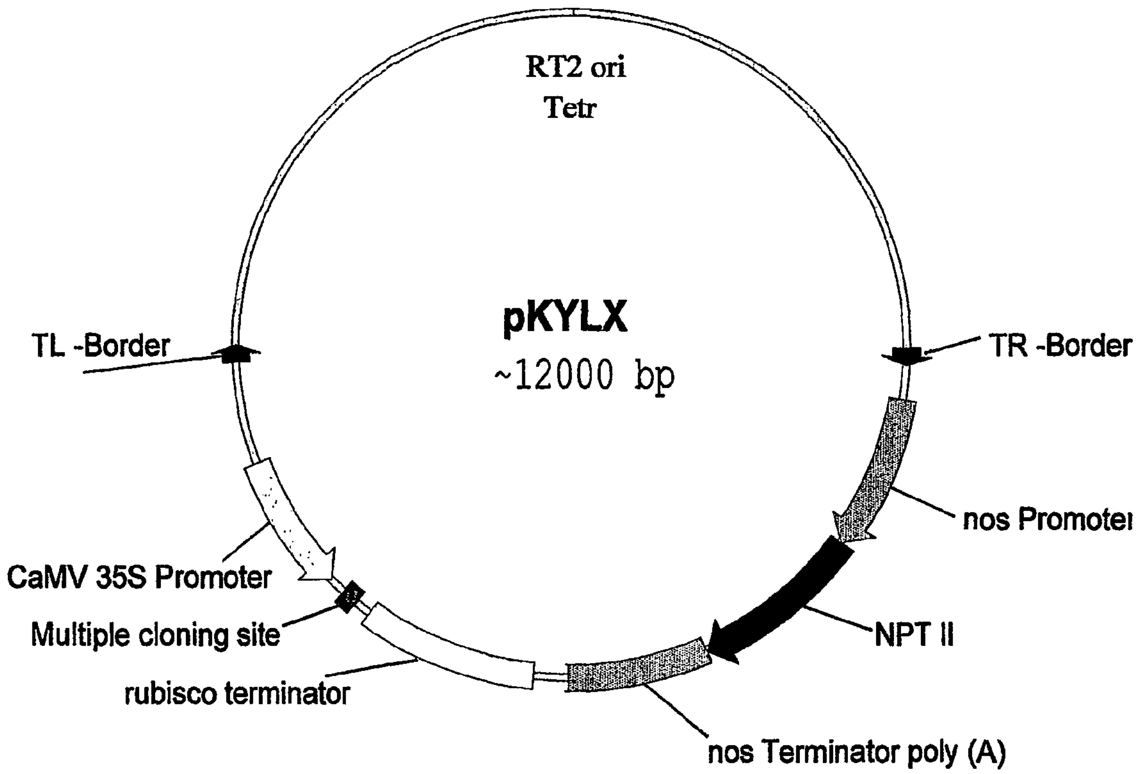
FIG. 2 shows the expression cassette of pKYLX71:35S2. TL, TR=left and right T-DNA borders (see An et al. for a detailed description of their origin). The multiple cloning site for pKYLX71 and pKYLX71:35S2 (the plasmids that were used) is: HindIII*-BamHI-XhoI*-PstI-SacI*-XbaI* (* indicates unique sites). The promoter in pKYLX71:35S2 is a 35S promoter modified by a duplicated "enhancer" region. Arrows indicate the direction of transcription for the expression cassette and NPTII gene. The plasmid confers tetracycline and kanemycin resistance upon *E. coli* and *Agrobacterium tumefaciens.*

A polynucleotide (SEQ ID NO. 4) from a truncated Rep gene from TYLCV-Is was prepared. The truncated Rep gene was PCR-amplified from the virus using primers EH312 and EH313 and cloned using standard methods known in the art. The nucleotide sequences of primer pair EH312 and EH313 are:

```
                                        (SEQ ID NO.1)
EH312:
5' CCA AGC TTA GCC ATT AGG TGT CCA AG 3' Hind III

                                        (SEQ ID NO.2)
EH313:
5' CTC TCG AGG GAT TTA CTG CCT GAA TTG 3' Xho I
```

cDNA clones of the truncated Rep gene were incorporated into a multiple cloning site of the binary vector pKYLX71: 35S2 containing the enhanced 35S promoter and rbcS-E9 terminator signal (see FIG. 2). The Rep gene fragment was then incorporated into the genome of tomato (*Lycopersicon esculentum* Mill.) by standard *Agrobacterium*-mediated transformation. *Agrobacterium*-mediated transformation of tomato was performed using standard protocols (Armitage et al., 1988; McCormick et al., 1986). Transgenic plants were screened by NPT II selection and the presence of the transgene was confirmed by PCR amplification.

EXAMPLE 2

TYLCV-Is Resistance in Tomato Plant

Seeds harvested from transformed plants were planted, and $T_1$ generation seedlings were inoculated with TYLCV-Is by whitefly-transmission. At harvest (12 weeks after inoculation), more than 41% of the plants in eight out of 30 $T_1$ lines remained free of virus symptoms, while 100% of the non-transformed control plants developed severe symptoms (Table 1). The results indicated that the exemplified truncated Rep gene of 508 nt confers high levels of resistance to TYLCV-Is (Florida isolate) in transgenic tomato plants. In addition, the phenotype of the transformed plants was normal in almost all plants.

The $T_2$ generation of TYLCV truncated Rep plants was exposed to viruliferous whiteflies prior to planting in the field during the fall of 2000 and spring 2001 at Bradenton, Fla. The TYLCV resistance observed in the greenhouse experiments also was evident under the harsher conditions present in the field conditions (Table 2, FIG. 4).

EXAMPLE 3

TYLCV-Is Resistance in Tobacco Plant

In order to test whether the truncated TYLCV Rep gene was effective in other plants *Nicotiana tabacum* cv. "Xanthi" was transformed with the same vector construct (FIG. 1) as done with tomatoes. Seven lines transformed with the truncated Rep gene showed immunity to TYLCV in tobacco. This demonstrated the resistance induced by the truncated Rep gene in a different host and in independent transformation events. No resistance was found to two other begomoviruses, cabbage leaf curl virus and tomato mottle virus (ToMoV). The mechanism of resistance induced by truncated Rep gene appeared to be due to gene silencing. This was based on Northern blots of transformed tobacco that indicated a suppression of the truncated Rep gene transcripts when the TYLCV resistant plants were challenged with TYLCV.

EXAMPLE 4

Assay of Rep and C4 Constructs in Tomato

Eight constructs containing either a TYLCV Rep gene, a TYLCV-Is C4 gene (a gene which is located within the Rep gene in a different reading frame), or modified or truncated forms of the Rep gene were evaluated in plants. The $T_1$ generation was inoculated using whiteflies reared on TYLCV-infected tomato plants. No symptoms were observed and TYLCV-Is (by both hybridization and PCR) was not detected in plants from three of the eight constructs (apparent immunity) (Table 1). All plants had normal phenotypes. Progeny of selected $T_1$ generation plants were inoculated with TYLCV and were evaluated in the field. As expected, plants in the $T_2$ generation segregated for resistance (Table 2). Two types of resistance were observed in the field plants—immunity and recovery. The phenotype of all resistant plants was normal. Plants were tested three times during the growing season for TYLCV-Is.

C4 and ΔC4 Constructs. Two constructs that contained the C4 gene that begins about 220 nt into the Rep gene, either in the sense (C4) or antisense orientation (ΔC4), and did not contain the intergenic region (IR) were evaluated. These produced no resistance in the $T_1$ generation (Table 1).

C1, ΔC1, NC1, and NΔC1 Constructs. Constructs that contained the intergenic region and the entire Rep gene either in the sense (C1 or antisense direction (ΔC1) did not produce immunity in the $T_1$ generation. Preliminary data suggests that this was independent of promoter (enhanced promoter: C1 and ΔC1 vs nonenhanced promoter: NC1 and NΔC1) although data on non-enhanced lines is still being collected. However, recovery was seen in the $T_1$ and $T_2$ generation plants transformed with NC1 and NΔC1, suggesting that the promoter had some effect.

2/5 TYLCV Rep and AS 2/5 TYLCV Rep Constructs. The best resistances were obtained using constructs that contained the TYLCV-Is IR and 2/5 of the TYLCV Rep gene begining with the 5' end of the Rep in either the sense (2/5 TYLCV Rep construct; SEQ ID NO. 6) or antisense (AS 2/5 TYLCV Rep construct; SEQ ID NO. 7) orientation (see Tables 1, 2, 3, and 4). The highest frequencies of immunity were observed with the 2/5 TYLCV Rep construct. This resistance appeared to be immunity and was observed at high frequency in the $T_1$ through $T_3$ generations. Some low rates of recovery were observed in the $T_2$ generation but even lower rates of recovery were. observed in the $T_3$ generation ($T_3$ generation data not shown).

EXAMPLE 5

Establishing TYLCV Rep Derived Immunity

Many plants in both the $T_1$ and $T_2$ generations transformed with the 2/5 TYLCV Rep construct showed no symptoms and no viral DNA (based on nucleic acid hybridization and PCR) after inoculation with TYLCV even when plants were tested at 3 times (4, 8, and 12 weeks after inoculation) during the growing season.

Studies were conducted to determine if virus levels were too low to detect by laboratory assays. Cuttings from susceptible plants (scions) were grafted on to inoculated transformed plants in which viral DNA could not be detected. No symptoms were present and no DNA was detected in the scions 4 weeks after the graft was established. This is in contrast to the same experiments in which susceptible scions were grafted onto non-transformed inoculated plants. These scions showed symptoms within 2-3 weeks after grafting. This strongly suggests that no virus was present in the inoculated plants, and that the mechanism of resistance prevents virus replication.

EXAMPLE 6

Transformation of Tobacco

The 2/5 TYLCV Rep construct was transformed into tobacco (*Nicotiana tabacum*) (Freitas-Astua, J., 2001). $T_1$ generation plants were tested for transgene copy number, for transcript production, and for resistance to TYLCV, and to two unrelated bipartite begomoviruses: Tomato mottle virus (ToMoV), and Cabbage leaf curl virus (CabLCV). Plants were determined to be immune to TYLCV, as evidenced by the lack of detection of virus by ELISA, PCR and nucleic acid hybridization after inoculation. This resistance was independent of transgene copy number. Transcripts were produced and transcript production was significantly reduced by challenge with TYLCV (FIGS. 5A and 5B). Transformed plants were not resistant to either ToMoV or CabCLV.

It should be understood that the examples and embodiments described herein are for illustrative purposes only and that various modifications or changes in light thereof will be suggested to persons skilled in the art and are to be included within the spirit and purview of this application.

TABLE 1

Evaluation of $T_1$ Generation Tomato Plants Transformed with Eight Different TYLCV Gene Constructs for Resistance to Infection by TYLCV.

| Transgene | No. $T_0$ Gen. Plants that Prod. Seed | No. $T_1$ Gen. Plants Evaluated[1] | No. Lines Tested | No. Lines with Transgene | No. Lines With Transgene And Immunity | Freq. of Immunity (%) | Mean Freq. of Immunity (%) |
|---|---|---|---|---|---|---|---|
| 2/5 TYLCV Rep | 50 | 455 | 35 | *30*[2] | 22 | 7-91 | 45.6 |
| AS-2/5 TYLCV Rep | 22 | 263 | 22 | *17* | *14* | 8-50 | 17.1 |
| C1ΔC1T2 | 15 | 175 | 15 | *10* | 3 | 7-86 | 47.3 |

TABLE 1-continued

Evaluation of $T_1$ Generation Tomato Plants Transformed with Eight Different TYLCV Gene Constructs for Resistance to Infection by TYLCV.

| Transgene | No. $T_0$ Gen. Plants that Prod. Seed | No. $T_1$ Gen. Plants Evaluated[1] | No. Lines Tested | No. Lines with Transgene | No. Lines With Transgene And Immunity | Freq. of Immunity (%) | Mean Freq. of Immunity (%) |
|---|---|---|---|---|---|---|---|
| ΔC4 | 18 | 197 | 18 | *12* | 0 | 0 | 0 |
| C4 | 1 | 12 | 1 | 0 | 0 | 0 | 0 |
| C1 | 2 | 28 | 2 | 1 | 0 | 0 | 0 |
| NC1 | 8 | 95 | 8 | *0* | *0* | *0* | 0 |
| NΔC1 | 5 | 67 | 5 | *0* | *0* | *0* | 0 |
| TOTAL | 123 | 1,292 | 106 | | | | |

[1]Excludes plants that died during the evaluation.
[2]Data in italics is not final and is still under investigation.

TABLE 2

Evaluation of $T_2$ Generation Tomato Plants Transformed with Different TYLCV Gene Constructs for Resistance to Infection by TYLCV.

| Construct | No. Lines Tested | No. of Plants Tested[1] | No. Lines with Immunity | Freq. of Immunity | Mean Freq. of Immunity | No. Lines with Recovery | Freq. of Recovery | Mean Freq. of Recovery |
|---|---|---|---|---|---|---|---|---|
| 2/5 TYLCV Rep | 13 | 347 | 13 | 26.6-80.0 | 53.8 | 5 | 3.3-31.8 | 13.7 |
| AS-2/5 TYLCV Rep | 5 | 135 | 5 | 10.0-55.1 | 22.3 | 4 | 16.6-40.0 | 29.2 |
| C1ΔC1T2 | 2 | 50 | 2 | 66.9-72.2 | 69.6 | 1 | 13.3 | 13.3 |
| ΔC4 | NT | | | | | | | |
| C4 | NT | | | | | | | |
| C1 | NT | | | | | | | |
| NC1 | 1 | 22 | 0 | — | — | 1 | 36.3 | 36.3 |
| NΔC1 | 2 | 29 | 0 | — | — | 2 | 31.8, 100 | 65.9 |
| TOTAL | | | | | | | | |

[1]Excludes plants that died during the evaluation.

TABLE 3

Evaluation of $T_2$ Generation 2/5 TYLCV Rep Construct for Resistance to Infection by TYLCV.

| Line No. | No. Plants Tested[1] | Freq. of Immunity in Line (%) | No. Plants with Transgene | Freq. of Immunity in Plants with Transgene (%) | % Recovery | % Escapes[2] |
|---|---|---|---|---|---|---|
| 2-5 | 29 | 75.9 | 18 | 100 | 0 | *18.0* |
| 2-9 | 30 | 80.0 | 23 | 100 | 0 | 0 |
| 21-2 | *44*[3] | *41.0* | | | — | |
| 21-4 | 30 | 80.0 | 24 | 100 | 0 | 0 |
| 21-8 | 29 | 55.1 | 12 | 92 | 0 | *33.3* |
| 21-10 | *20* | *39.0* | | | — | |
| 23-2 | *44* | *27.0* | | | — | |
| 23-5 | 12 | 31.8 | 5 | 100 | 0 | *29.0* |
| 23-7 | *36* | *32.0* | | | — | |
| 25-4 | *22* | *57.0* | | | — | |
| 25-5 | 30 | 40.0 | 12 | 83.3 | 0 | *6.6* |
| 25-11 | 28 | 39.2 | 12 | 58.3 | 0 | *10.7* |
| 25-15 | *12* | *27.0* | | | — | |
| 32-6 | *39* | *40.0* | | | — | |
| 32-12 | *18* | *29.0* | | | — | |
| 37-6 | *40* | *40.0* | | | — | |
| 37-11 | *38* | *78.0* | | | — | |
| 37-12 | 30 | 33.3 | 13 | 76.9 | 23.0 | *6.6* |
| 37-13 | *31* | *52.0* | | | — | |
| 45-10 | 25 | 80.0 | 19 | 100 | 0 | *4.0* |
| 51-4 | 30 | 26.6 | 10 | 80 | 20.0 | 0 |
| 62-5 | 29 | 48.2 | 13 | 100 | 0 | *3.4* |

TABLE 3-continued

Evaluation of $T_2$ Generation 2/5 TYLCV Rep Construct for Resistance to Infection by TYLCV.

| Line No. | No. Plants Tested[1] | Freq. of Immunity in Line (%) | No. Plants with Transgene | Freq. of Immunity in Plants with Transgene (%) | % Recovery | % Escapes[2] |
|---|---|---|---|---|---|---|
| 70-12 | 23 | 82.6 | 13 | 69 | 0 | *13.0* |
| 89-5 | 22 | 27.2 | 5 | 100 | 0 | *4.5* |

[1]Excludes plants that died during the evaluation.
[2]% Escapes - plants with no virus but no transgene was detected. (These are being re-evaluated with primers 28 and 94 that bind in the transformation vector and outside the TYLCV gene.)
[3]Data in italics is not final and is still under investigation.

TABLE 4

Evaluation of $T_2$ generation plants transformed with AS-2/5 TYLCV Rep construct for Resistance to Infection by TYLCV.

| Line No. | No. Plants Tested[1] | Freq. of Immunity in Line (%) | No. Plants with Transgene | Freq. of Immunity in Plants with Transgene (%) | % Recovery | % Escapes[2] |
|---|---|---|---|---|---|---|
| 66-2 | 30 | 10.0 | 8 | 12.5 | 37.5 | 0 |
| 66-7 | 29 | 55.1 | 15 | 73.3 | 0 | 0 |
| 66-11 | 30 | 20.0 | 18 | 22.2 | 66.6 | *3.3* |
| 84-1 | 22 | 18.1 | 8 | 37.5 | 50.0 | *10.0* |
| 84-8 | 24 | 8.3 | 6 | 0.0 | 66.6 | 0 |

[1]Excludes plants that died during the evaluation.
[2]% Escapes - plants with no virus but no Transgene. (These are being re-evaluated with primers 28 and 94 that bind in the transformation vector but not the TYLCV gene.)
[3]Data in italics is not final and is still under investigation.

REFERENCES

An, G., B. Watson, S. Stachel, M. P. Gordon and E. W. Nester (1985) "New cloning vehicles for transformation of higher plants" *EMBO J.* 4:277-284.

Arguello-Astorga, G. R. (2001) "An Iteron-Related Domain is Associated to Motif 1 in the Replication Proteins of Geminiviruses: Identification of Potential Interacting Amino Acid-Base Pairs by a Comparative Approach" *Arch Virol* 146:1465-1485.

Armitage, P., R. Walden & J. Draper (1988) "Vectors for transformation of plant cells using *Agrobacterium" Plant Genetic Transformation and Gene Expression—A Laboratory Manual*, J. Draper, R. Scott, P. Armitage, R. Walden, eds. Blackwell Scientific Publications, Oxford, pages 1-16.

Altschul et al. (1990) i J. Mol Biol. 215:402-410.

Altschul et al. (1997) *Nucl Acids Res.* 25:3389-3402.

Beltz, G. A., K. A. Jacobs, T. H. Eickbush, P. T. Cherbas, and F. C. Kafatos (1983) *Methods of Enzymology*, R. Wu, L. Grossman and K. Moldave [eds.] Academic Press, New York 100:266-285.

Bendahmane, M. and B. Gronenborn (1997) "Engineering Resistance Against Tomato Yellow Leaf Curl Virus (TYLCV) using antisense RNA" *Plant Moleczilar Biology* 33:351-357.

Brunetti, A., M. Tavazza, E. Noris, R. Tavazza, P. Caciagli, G. Ancora, S. Crespi G. P. Accotto (1997) "High expression of truncated viral Rep protein confers resistance to tomato yellow leaf curl virus in transgenic tomato plants" *Mol. Plant-Microbe Interact* 10:571-579.

Cahill, M., K. Gorman, S. Kay, I. Denholm (1996) "Baseline determination and detection of resistance to imidacloprid in *Bemisia tabaci* (Homoptera:Aleyrodidae)" *Bull. of Ento. Res.* 86:343-349.

Carrer, H., P. Maliga (1995) "Targeted insertion of foreign genes into the tobacco plastid genium without physical linkage to the selectable marker" *Biotechnology* 13:791-794.

Fauquet, M. C. and M. A. Mayo (1999) "Abbreviations for plant virus names—1999" *Arch. Virol.* 144:1249-1273.

Freitas-Astua, J. (2001) "Characterization of Resistance In Transgenic Tobacco Plants Expressing Begomoviruses Genes," Ph.D. Dissertation, Gainesville, University of Florida.

Hanson, S. F., D. P. Maxwell (1999) "trans-Dominant inhibition of gerniniviral DNA replication by bean golden mosaic geminivirus rep gene mutants" *Phytopathology* 89:480-486.

Hong, Y., J. Stanley (1996) "Virus resistance in *Nicotiana benthamiana* conferred by African cassava mosaic virus replication-associated protein (AC1) transgene" *Mol. Plant-Microbe Interact* 9:219-225.

Karlin and Altschul (1990) *Proc. Natl. Acad. Sci. USA* 87:2264-2268.

Karlin and Altschul (1993) *Proc. Natl. Acad. Sci USA* 90:5873-5877.

Kelemen, Z. et al. (2002) "Transformation Vector Based on Promoter and Intron Sequences of a Replacement Histone H3 Gene. A Tool for High, Constitutive Gene Expression in Plants" *Transgenic Research* 11:69-72.

Lapidot, M. M. Friedmann, M. Pilowsky, R. Ben-Joseph, S. Cohen (2001) "The Effect of Host Resistance on *Tomato*

*Yellow Leaf Curl Virus* (TYLCV) on Virus Acquisition and Transmission by its Whitefly Vector" *Phytopathology* 91(12):1209-1213.

Maniatis, T., E. F. Fritsch, J. Sambrook (1982) *Molecular Cloning: A Laboratory Manual*, Cold Spring Harbor Laboratory, Cold Spring Harbor, N.Y.

McCormick, S., Niedermeyer, J., Fry, J., Barnason, A., Horsch, R, & Fraley, R. (1986) "Leaf disc transformation of cultivated tomato (*L. esculentum*) using *Agrobacterium tumefaciens" Plant Cell Reports* 5:81-84.

Noris, E., G. Accotto, R. Tavazza, A. Brunetti, S. Crespi, M. Tavazza (1996) "Resistance to tomato yellow leaf curl geminivirus in *Nicotiana benthaminana* plants transformed with a truncated viral C1 gene" *Virology* 224(1): 130-138.

Polston, J. E. and P. K. Anderson (1997) "The emergence of whitefly-transmitted gemini-viruses in tomato in the Western hemisphere" *Plant Disease* 81:1358-1369.

Polston, J. E., R. J. McGovern, L. G. Brown (1999) "The appearance of tomato yellow leaf curl virus in Florida and implications for the spread of the and other geminiviruses in the U.S." *Plant Dis.* 83:984-988.

Schardl, C., A. D. Byrd, G. B. Benzion, M. A. Altschuler, D. F. Hildebrand, A.G. Hunt (1987) "Design and construction of a versatile system for the expression of foreign genes in plants" *Gene* 61:1-11.

Stout, J. T., H. T. Lui, J. E. Polston, R. L. Gilbertson, M. K. Nakhia, S. F. Hanson, D. P. Maxwell (1997) "Engineered rep gene-mediated resistance to tomato mottle geminivirus in tomato" *Phytopathology* 87:S96.

Williams, L., T. J. Dennehy, J. C. Palumbo (1996) "Development of a resistance management program for imidacloprid" Proc. Beltwide Cotton Conferences pp. 752-755.

Wei, C.-F., G. A. Alianell, G. H. Bencen, H. B. Gray, Jr. (1983) "Isolation and Comparison of Two Molecular Species of the BAL31 Nuclease from *Alteromonas espejiana* with Distinct Kinetic Properties" *The Journal of Biological Chemistry* 258(22):13506-13512.

Zuo, J. et al. (2002) "Marker-free Transformation: Increasing Transformation Frequency by the Use of Regeneration-Promoting Genes" *Current Opinion in Biotechnology* 13:173-180.

We claim:

1. A method for providing resistance to infection by a tomato yellow leaf curl virus-Israel (TYLCV-Is) in a plant or plant tissue, said method comprising incorporating in or transforming said plant or plant tissue with a polynucleotide selected from the group consisting of:

i) a polynucleotide comprising a fragment of a TYLCV Rep gene, wherein said polynucleotide comprising a fragment of said TYLCV Rep gene comprises the nucleotide sequence shown in SEQ ID NO. 4; and ii) a polynucleotide comprising a sequence that is antisense to said fragment of said TYLCV Rep gene, wherein said polynucleotide comprising a sequence that is antisense to said fragment of said TYLCV Rep gene comprises the nucleotide sequence shown in SEQ ID NO. 5, wherein resistance to TYLCV-Is infection exhibited by said plant or plant tissue comprising said polynucleotide is due to expression of said polynucleotide.

2. The method according to claim 1, wherein said plant or plant tissue is selected from the group consisting of tomato, tobacco, statice, petunia, lisianthus, and tomatillo.

3. The method according to claim 2, wherein said plant or plant tissue is tomato.

4. The method according to claim 2, wherein said plant or plant tissue is tobacco.

5. The method according to claim 1, wherein said plant or plant tissue is transformed with said polynucleotide by agroinfection, biolistic targeting, electroporation, or direct gene injection.

6. The method according to claim 1, wherein said polynucleotide comprises regulatory sequences operably linked to said Rep gene sequence.

7. The method according to claim 6, wherein said regulatory sequences comprise a promoter.

8. The method according to claim 7, wherein said promoter is selected from the group consisting of constitutive promoter, tissue-specific promoter, and inducible promoter.

9. The method according to claim 7, wherein said promoter is selected from the group consisting of CaMV 35S promoter, CaMV 35S2 promoter, octopine synthase promoter, nopaline synthase promoter, Ap3 promoter, heat shock 80 promoter, alfalfa histone H3.2 gene promoter, and E8 promoter.

10. The method according to claim 1, wherein said polynucleotide comprises a selectable marker gene.

11. The method according to claim 10, wherein said selectable marker gene provides for antibiotic resistance when expressed.

12. The method according to claim 11, wherein said antibiotic resistance is selected from the group consisting of resistance to G418, hygromycin, bleomycin, kanamycin, and gentamicin.

13. The method according to claim 1, wherein said polynucleotide comprises a 3' non-translated termination sequence.

14. A transgenic or transformed plant or plant tissue having increased resistance to infection by a tomato yellow leaf curl virus-Israel (TYLCV-Is) wherein said plant or plant tissue comprises a polynucleotide selected from the group consisting of:

i) a polynucleotide comprising a fragment of a TYLCV Rep gene, wherein said polynucleotide comprising a fragment of said TYLCV Rep gene comprises the nucleotide sequence shown in SEQ ID NO. 4; and ii) a polynucleotide comprising a sequence that is antisense to said fragment of said TYLCV Rep gene, wherein said polynucleotide comprising a sequence that is antisense to said fragment of said TYLCV Rep gene comprises the nucleotide sequence shown in SEQ ID NO. 5, wherein resistance to TYLCV-Is infection exhibited by said plant or plant tissue comprising said polynucleotide is due to expression of said polynucleotide.

15. The plant or plant tissue according to claim 14, wherein said plant or plant tissue is selected from the group consisting of tomato, tobacco, statice, petunia, lisianthus, and tomatillo.

16. The plant or plant tissue according to claim 15, wherein said plant or plant tissue is tomato.

17. The plant or plant tissue according to claim 15, wherein said plant or plant tissue is tobacco.

18. The plant or plant tissue according to claim 14, wherein said plant or plant tissue is transformed with said polynucleotide by agroinfection, biolistic targeting, electroporation, or direct gene injection.

19. The plant or plant tissue according to claim 14, wherein said polynucleotide comprises regulatory sequences operably linked to said Rep gene sequence.

20. The plant or plant tissue according to claim 19, wherein said regulatory sequences comprise a promoter.

21. The plant or plant tissue according to claim 20, wherein said promoter is selected from the group consisting of constitutive promoter, tissue-specific promoter, and inducible promoter.

22. The plant or plant tissue according to claim 20, wherein said promoter is selected from the group consisting of CaMV 35S promoter, CaMV 35S2 promoter, octopine synthase promoter, nopaline synthase promoter, Ap3 promoter, heat shock 80 promoter, alfalfa histone H3.2 gene promoter, and E8 promoter.

23. The plant or plant tissue according to claim 14, wherein said polynucleotide comprises a selectable marker gene.

24. The plant or plant tissue according to claim 23, wherein said selectable marker gene provides for antibiotic resistance when expressed.

25. The plant or plant tissue according to claim 24, wherein said antibiotic resistance is selected from the group consisting of resistance to G418, hygromycin, bleomycin, kanamycin, gentamicin.

26. The plant or plant tissue according to claim 14, wherein said polynucleotide comprises a 3' non-translated termination sequence.

27. A progeny of the plant or plant tissue of claim 14, wherein said progeny comprises said polynucleotide.

28. A plant cell comprising in its genome a polynucleotide selected from the group consisting of:

i) a polynucleotide comprising a fragment of a TYLCV Rep gene, wherein said polynucleotide comprising a fragment of said TYLCV Rep gene comprises the nucleotide sequence shown in SEQ ID NO. 4; and ii) a polynucleotide comprising a sequence that is antisense to said fragment of said TYLCV Rep gene, wherein said polynucleotide comprising a sequence that is antisense to said fragment of said TYLCV Rep gene comprises the nucleotide sequence shown in SEQ ID NO. 5, wherein resistance to TYLCV-Is infection exhibited by said plant or plant tissue comprising said polynucleotide is due to expression of said polynucleotide.

29. A plant seed comprising in its genome a polynucleotide selected from the group consisting of:

i) a polynucleotide comprising a fragment of a TYLCV Rep gene, wherein said polynucleotide comprising a fragment of said TYLCV Rep gene comprises the nucleotide sequence shown in SEQ ID NO. 4; and ii) a polynucleotide comprising a sequence that is antisense to said fragment of said TYLCV Rep gene, wherein said polynucleotide comprising a sequence that is antisense to said fragment of said TYLCV Rep gene comprises the nucleotide sequence shown in SEQ ID NO. 5, wherein resistance to TYLCV-Is infection exhibited by said plant or plant tissue comprising said polynucleotide is due to expression of said polynucleotide.

30. The method according to claim 1, wherein said fragment of said TYLCV Rep gene comprises the upstream intergenic region of said Rep gene.

31. The plant or plant tissue according to claim 14, wherein said fragment of said TYLCV Rep gene comprises the upstream intergenic region of said Rep gene.

32. The plant cell according to claim 28, wherein said fragment of said TYLCV Rep gene comprises the upstream intergenic region of said Rep gene.

33. The plant seed according to claim 29, wherein said fragment of said TYLCV Rep gene comprises the upstream intergenic region of said Rep gene.

34. The method according to claim 1, wherein said method further comprises growing a plant from said plant or plant tissue that has incorporated or been transformed with said polynucleotide.

35. The method according to claim 1, wherein said polynucleotide comprises a fragment of a TYLCV Rep gene, wherein said polynucleotide comprising a fragment of said TYLCV Rep gene comprises the nucleotide sequence shown in SEQ ID NO. 4.

36. The method according to claim 1, wherein said polynucleotide comprises a sequence that is antisense to said fragment of said TYLCV Rep gene, wherein said polynucleotide comprising a sequence that is antisense to said fragment of said TYLCV Rep gene comprises the nucleotide sequence shown in SEQ ID NO. 5.

37. The plant or plant tissue according to claim 14, wherein said polynucleotide comprises a fragment of a TYLCV Rep gene, wherein said polynucleotide comprising a fragment of said TYLCV Rep gene comprises the nucleotide sequence shown in SEQ ID NO. 4.

38. The plant or plant tissue according to claim 14, wherein said polynucleotide comprises a sequence that is antisense to said fragment of said TYLCV Rep gene, wherein said polynucleotide comprising a sequence that is antisense to said fragment of said TYLCV Rep gene comprises the nucleotide sequence shown in SEQ ID NO. 5.

39. The plant cell according to claim 28, wherein said polynucleotide comprises a fragment of a TYLCV Rep gene, wherein said polynucleotide comprising a fragment of said TYLCV Rep gene comprises the nucleotide sequence shown in SEQ ID NO. 4.

40. The plant cell according to claim 28, wherein said polynucleotide comprises a sequence that is antisense to said fragment of said TYLCV Rep gene, wherein said polynucleotide comprising a sequence that is antisense to said fragment of said TYLCV Rep gene comprises the nucleotide sequence shown in SEQ ID NO. 5.

41. The plant seed according to claim 29, wherein said polynucleotide comprises a fragment of a TYLCV Rep gene, wherein said polynucleotide comprising a fragment of said TYLCV Rep gene comprises the nucleotide sequence shown in SEQ ID NO. 4.

42. The plant seed according to claim 29, wherein said polynucleotide comprises a sequence that is antisense to said fragment of said TYLCV Rep gene, wherein said polynucleotide comprising a sequence that is antisense to said fragment of said TYLCV Rep gene comprises the nucleotide sequence shown in SEQ ID NO. 5.

43. A plant or plant tissue produced by the method of claim 1.

44. The plant or plant tissue according to claim 43, wherein said plant or plant tissue is selected from the group consisting of tomato, tobacco, statice, petunia, lisianthus, and tomatillo.

45. The plant or plant tissue according to claim 44, wherein said plant or plant tissue is tomato.

46. The plant or plant tissue according to claim 44, wherein said plant or plant tissue is tobacco.

* * * * *

UNITED STATES PATENT AND TRADEMARK OFFICE

CERTIFICATE OF CORRECTION

PATENT NO. : 7,531,716 B2 Page 1 of 1
APPLICATION NO. : 10/477240
DATED : May 12, 2009
INVENTOR(S) : Jane E. Polston and Ernest Hiebert It is certified that error appears in the above-identified patent and that said Letters Patent is hereby corrected as shown below:

<u>Column 2,</u>
Line 2, “the United States Florida,” should read --the United States (Florida,--.
Lines 23-24, “Kansas City, Mo.)” should read --Kansas City, MO)--.

<u>Column 4,</u>
Line 15, “with TYLCV.FIG” should read --with TYLCV. FIG--.

<u>Column 7,</u>
Line 39, “the 35S or 35S2 promoter” should read --the 35S or $35S^2$--.

<u>Column 9,</u>
Line 27, “NCB/NIH” should read --NCBI/NIH--.
Lines 32-33, “Maniatis, T. et al., 1982)” should read --(Maniatis, T. et al., 1982)--.

<u>Column 11,</u>
Line 31, “sense (C1 or” should read --sense (C1) or--.
Line 41, “Rep gene begining” should read --Rep gene beginning--.

<u>Column 12,</u>
Lines 1-2, “recovery were. observed” should read --recovery were observed--.

<u>Column 15,</u>
Line 51, “Altschul et al. (1990) i J. Mol.” should read --Altschul et al. (1990) J. Mol.--.
Line 60, “Plant Moleczilar Biology” should read --Plant Molecular Biology--.

Signed and Sealed this

Fifteenth Day of September, 2009

David J. Kappos
*Director of the United States Patent and Trademark Office*